(12) United States Patent
Padgurskas et al.

(10) Patent No.: US 8,297,104 B2
(45) Date of Patent: Oct. 30, 2012

(54) DEVICE FOR MEASURING THE INFLUENCE OF FRICTION FORCE ON THE WEAR CHARACTERISTICS OF A MATERIAL SURFACE

(75) Inventors: Juozas Padgurskas, Kauno r. (LT); Albinas Andriusis, Kaunas (LT)

(73) Assignee: Lithuanian University of Agriculture, Akademijos mst., Kauno r.

( * ) Notice: Subject to any disclaimer, the term of this patent is extended or adjusted under 35 U.S.C. 154(b) by 245 days.

(21) Appl. No.: 12/919,672

(22) PCT Filed: Feb. 25, 2009

(86) PCT No.: PCT/LT2009/000003
§ 371 (c)(1),
(2), (4) Date: Aug. 26, 2010

(87) PCT Pub. No.: WO2009/108031
PCT Pub. Date: Sep. 3, 2009

(65) Prior Publication Data
US 2011/0000278 A1    Jan. 6, 2011

(30) Foreign Application Priority Data
Feb. 29, 2008   (LT) ...................................... 2008 017

(51) Int. Cl.
*G01N 19/02*        (2006.01)
(52) U.S. Cl. ................................................. 73/9; 73/10
(58) Field of Classification Search .................... 73/9, 10
See application file for complete search history.

(56) References Cited

U.S. PATENT DOCUMENTS

| 4,958,511 A | 9/1990 | Marcus |
| 5,837,882 A | 11/1998 | Bacigalupo et al. |
| 5,996,395 A | 12/1999 | Nagasawa et al. |

FOREIGN PATENT DOCUMENTS

| JP | 2004039049 A | 2/2004 |
| SU | 86437 | 3/1949 |

(Continued)

OTHER PUBLICATIONS

Written Opinion of the International Search Authority for WO2009108031. Aug. 31, 2010.*

(Continued)

*Primary Examiner* — Lisa Caputo
*Assistant Examiner* — Punam Roy
(74) *Attorney, Agent, or Firm* — Rader, Fishman & Grauer PLLC; Alexander D. Rabinovich

(57) ABSTRACT

A device for the measurement of the influence of friction force on the wear characteristics of a material surface comprises a frame with a cover. A shaft is installed in the frame. A moveable element of a friction pair is fixed on the shaft. A holder of a pressed element of the friction pair and a clamp which applies a regulated load on the holder with the pressed friction element are installed in the cover. The holder of the pressed friction element is installed in a holder frame with first membranes which allow the motion only perpendicular to the axis of holder frame. The holder-frame is installed in the cover also with second membranes that allow it to move only in its axial direction. The system of the membranes damps the impact of inertial forces on the friction pair.

10 Claims, 1 Drawing Sheet

FOREIGN PATENT DOCUMENTS

SU    1174830 A1    8/1985

OTHER PUBLICATIONS

International Search Report from International Application No. PCT/LT 2009/000003 dated May 18, 2009 (1 page).

DGMK—Research Report 514, Hamburg, 1999. (12 pages).
English Abstract of SU-1174830-A1, Aug. 23, 1985.
English Abstract of JP-2004039049-A, Feb. 5, 2004.
English Abstract of SU-86437, 1949.

* cited by examiner

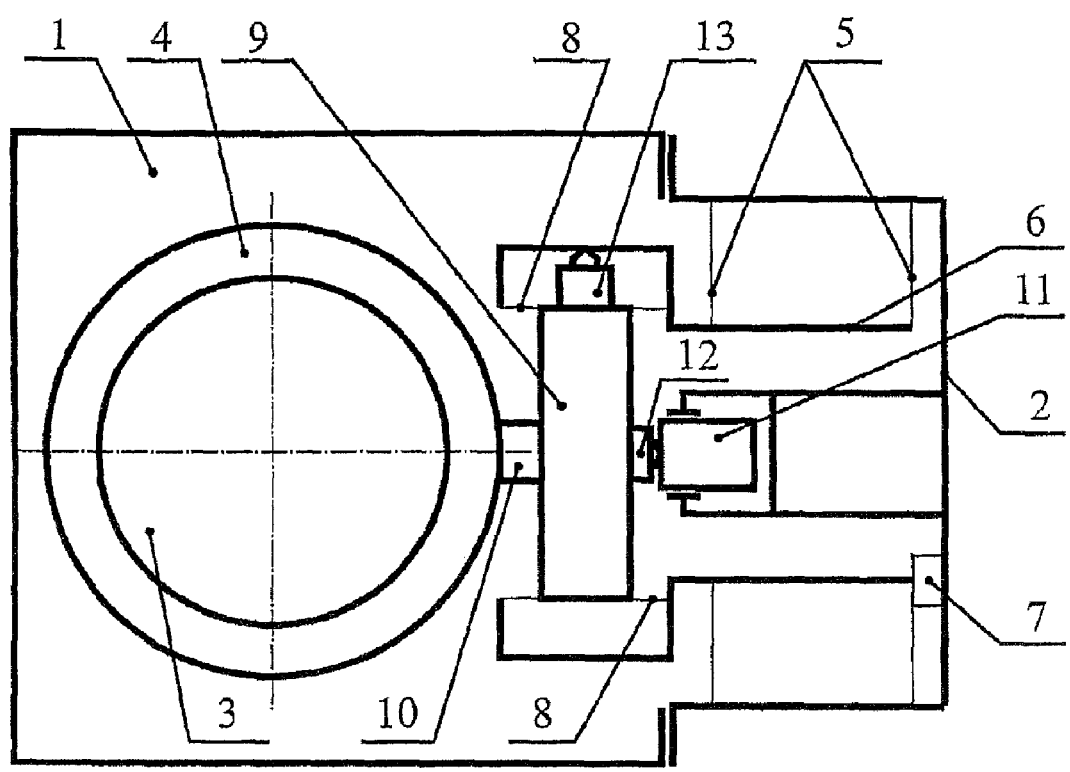

US 8,297,104 B2

DEVICE FOR MEASURING THE INFLUENCE OF FRICTION FORCE ON THE WEAR CHARACTERISTICS OF A MATERIAL SURFACE

CROSS-REFERENCE TO RELATED APPLICATIONS

This application is a U.S. National phase application of the International application WO 2009/108031 A1 (PCT/LT2009/000003) and claims priority to Lithuanian application 2008 17, filed Feb. 29, 2008, the both applications being hereby incorporated by reference in their entirety.

BACKGROUND OF THE INVENTION

1. Field of the Invention

The invention generally relates to the area of wear measurement of material surface. More specifically, it relates to a device for measuring the effect of friction force on wear characteristics of a material surface and can find its use in machinery production technology.

2. Description of Related Art

Surface wear depends on the dynamic loads of interacting surfaces and lubricant properties. Different methods and devices are used for measuring wear.

Known in the art is a device for the measurement of variable loads characteristics of a sample (Mechanical testing of hydraulic fluids. DGMK-Research Report 514, Hamburg, 1999). A tested friction pair is loaded mechanically by an eccentric and by changing pressure in a hydraulic system of the device. The disadvantage of this device is the shock load caused by the eccentric at the start of pair friction and the impossibility to evaluate the influence of this shock load on wearing.

Also known is a wear measurement device of anodic aluminum surface (U.S. Pat. No. 4,958,511 published Sep. 25, 1990). The surface in this device is loaded by the pressing of ball and the ball rotation speed is measured. Wear depends not only on the ball pressure and its rotation speed but also on vibrations of device elements' interaction that are not considered.

There is also known a device for measuring fatigue characteristics of contacting surfaces (U.S. Pat. No. 5,837,882 published Nov. 17, 1998). The device is designed to measure surface fatigue characteristics depending on the force of contacting pressure and impact time. Balls located around a fixed round sample are supported by two rings with bevel internal surfaces. Approaching the bevel surfaces can gradually increase or decrease the load on the sample surface. The load is regulated. This device cannot estimate the value of surface abrasion but rather the beginning of surface decay.

The most relevant to the present invention is believed to be a device (U.S. Pat. No. 5,996,395 published Dec. 7, 1999) for the evaluation of friction interaction between a friction material as a sample and a slide portion which are in sliding contact. The sample is pressed on the sliding portion and the pressing force is measured. The frequency of actuated vibration is measured by changing sliding speed. This device measures pressing force and sliding speed but the settled loading mode is distorted by the elements' interaction vibrations which are measured but whose influence on the final wear results is not taken into consideration.

BRIEF SUMMARY OF THE INVENTION

The device according to the present invention avoids the above-mentioned disadvantages. Increased lateral inertial loads in the device are damped and settled regularity of the loading is obtained. It is achieved by providing the device in the form of a frame with a cover with an installed clamp for the transfer of a regulated force on a pressed friction element through a sensor. This pressed friction element interacts with the surface of a moveable friction element which is fixed to a rotating shaft. Pressed friction element is fixed to a holder which is installed in its frame with membranes and a holder frame is installed in the cover of the device with other membranes. The holder interacts with the frame through a sensor which is connected to a control board. The frame of the holder interacts with the device through a sensor of the friction element position connected to the control board.

BRIEF DESCRIPTION OF THE DRAWINGS

Further objectives, features, characteristics, and effects of the invention will be clear from the ensuing detailed description of its illustrative embodiment and accompanying drawings of FIG. 1 in which a sketch of the device according to the invention is presented.

DETAILED DESCRIPTION OF THE INVENTION

The device comprises a frame 1 and a cover 2. A shaft 3 is installed in the frame 1. A moveable friction element 4 is fixed on the shaft 3. A frame 6 is installed in the cover 2 with first membranes 5 and interacts with the cover 2 through a shift sensor 7. A-holder 9 is installed in the frame 6 with second membranes 8 and it keeps a pressed friction element 10. The pressed friction element 10 and moveable friction element 4 form a friction pair. A pressing force sensor 12 for the measurement of loading force is installed between the holder 9 and a clamp 11. The holder 9 interacts with the frame 6 through a friction force sensor 13.

The device operates as following. Shaft 3 with moveable friction element 4 begins to rotate against pressed friction element 10. Pressing force and its variation regularity is programmed and controlled through pressing force sensor 12, holder 9 and clamp 11. First membranes 5 allow frame 6 to move only along its axis (assumed horizontal in FIG. 1 and not shown), whereas second membranes 8 allow the motion of holder 9 only perpendicularly to the axis of frame 6. Pressing force sensor 12 transfers to a control board (not shown) a signal about variation of the pressing force in the friction pair, i.e. between friction elements 4 and 10, and friction force sensor 13 transfers a signal about the friction force. Shift sensor 7 measures a shift of frame 6 caused by wear of surfaces of friction elements 4 and 10.

The load in the device is applied on the friction elements 4 and 10 without any lateral interim chains of the motion. Therefore, the force pressing on holder 9, which is applied by clamp 11, is equal to the pressing load between friction elements 4 and 10. Settled loading regularity between friction elements 4 and 10 is sustained.

This device includes the case when pressed friction element 10 is fixed to holder 9 which moves by the alternating motion.

The efficiency of device is based on the absence of any interim chains which provides for raising lateral dynamic loads in the friction pair. The system of the membranes ensures the geometric stability of friction pair's contact and enables sustaining the settled regularity of the pressing force.

The invention claimed is:

1. A device for measuring the influence of friction force on the wear characteristics of a material surface, the device comprising a frame with a cover, a friction pair of a moveable friction element and a pressed friction element, and a clamp for applying a controlled force on the friction pair, the moveable friction element being installed on the frame, the pressed friction element being fixed to a holder, the holder being installed with first membranes on a holder frame, the holder frame being installed with second membranes in the cover, the clamp exerting pressure onto the pressed friction element through the holder.

2. The device according to claim 1, wherein the moveable friction element is fixed on a shaft whose rotation speed is regulated.

3. The device according to claim 1, wherein the holder frame interacts with the device through a first sensor connected to a control board.

4. The device according to claim 1, wherein the clamp interacts with the holder through a second sensor connected to a control board.

5. The device according to claim 1, wherein holder interacts with the holder frame through a third sensor connected to a control board.

6. A device according to claim 1, wherein the holder is adapted to move in alternating motion.

7. A device for measuring the influence of friction force on the wear characteristics of a material surface, the device comprising a frame with a cover, a friction pair of a moveable friction element and a pressed friction element, and a clamp for applying a controlled force on the friction pair, the moveable friction element being fixed on a regulated rotation speed shaft installed on the frame, the pressed friction element being fixed to a holder, the holder being installed with first membranes on a holder frame interacting with the holder frame through a friction force sensor connected to a control board, the holder frame being installed with second membranes in the cover interacting with the cover through a shift sensor connected to the control board, the clamp exerting pressure onto the pressed friction element through the holder thereof, a pressing force sensor being installed between the clamp and the holder.

8. A device according to claim 7, wherein the holder is adapted to move in alternating motion.

9. A device for measuring the influence of friction force on the wear characteristics of a material surface comprising:
  a frame with a cover,
  a friction pair of a moveable friction element and a pressed friction element,
  a holder, holding the pressed friction element, and
  a clamp for applying a controlled force on the friction pair,
  the holder being installed with first membranes on a holder frame interacting with the holder frame through a friction force sensor connected to a control board,
  the holder frame being installed with second membranes in the cover interacting with the cover through a shift sensor connected to the control board,
  the moveable friction element being fixed on a regulated rotation speed shaft installed on the frame,
  the clamp exerting pressure onto the pressed friction element through the holder thereof,
  a pressing force sensor being installed between the clamp and the holder,
  whereby the load is applied to the friction elements without intermediate chains of motion to
  thereby sustain settled loading regularity between the friction elements.

10. A device according to claim 9, wherein the holder is adapted to move in alternating motion.

* * * * *